US010201655B2

(12) United States Patent
O'Cearbhaill et al.

(10) Patent No.: US 10,201,655 B2
(45) Date of Patent: Feb. 12, 2019

(54) METHODS AND DEVICES FOR INSERTING A NEEDLE

(71) Applicants: The Brigham and Women's Hospital, Inc., Boston, MA (US); Massachusetts Institute of Technology, Cambridge, MA (US)

(72) Inventors: Eoin D. O'Cearbhaill, Cambridge, MA (US); Bryan Laulicht, Cambridge, MA (US); Alexander H. Slocum, Bow, NH (US); Robert S. Langer, Newton, MA (US); Omid C. Farokhzad, Chestnut Hill, MA (US); Jeffrey M. Karp, Brookline, MA (US)

(73) Assignees: The Brigham and Women's Hospital, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 233 days.

(21) Appl. No.: 14/421,267

(22) PCT Filed: Aug. 7, 2013

(86) PCT No.: PCT/US2013/053955
§ 371 (c)(1),
(2) Date: Feb. 12, 2015

(87) PCT Pub. No.: WO2014/028285
PCT Pub. Date: Feb. 20, 2014

(65) Prior Publication Data
US 2015/0209509 A1 Jul. 30, 2015

Related U.S. Application Data

(60) Provisional application No. 61/682,503, filed on Aug. 13, 2012.

(51) Int. Cl.
*A61M 5/158* (2006.01)
*A61B 17/34* (2006.01)
(Continued)

(52) U.S. Cl.
CPC ....... *A61M 5/1582* (2013.01); *A61B 17/3401* (2013.01); *A61B 17/3468* (2013.01);
(Continued)

(58) Field of Classification Search
CPC .. A61M 5/1582; A61M 5/162; A61M 5/3291; A61M 5/46; A61M 2005/1585;
(Continued)

(56) References Cited

U.S. PATENT DOCUMENTS 4,414,983 A   11/1983 Evans et al.
4,940,458 A    7/1990 Cohn
(Continued)

FOREIGN PATENT DOCUMENTS

WO   WO 2002/056937 A2   7/2002
WO   WO 2008/097609 A2   8/2008

OTHER PUBLICATIONS

International Search Report and Written Opinion for PCT/US2013/053955 dated Nov. 28, 2013.
(Continued)

*Primary Examiner* — Amber Stiles
(74) *Attorney, Agent, or Firm* — Wolf, Greenfield & Sacks, P.C.

(57) ABSTRACT

An apparatus provides targeted placement of openings for infusing fluids into a body. The apparatus provides a driving force to a penetrating medical device, such as a needle, when the apparatus tip encounters material of high resistance. When the apparatus tip encounters a low resistance material, no further driving force is applied to the apparatus due to contraction of an element made of interlaced flexible ele-
(Continued)

ments. A multi-opening needle is provided in some embodiments wherein placement of one of the openings in a target region with a relatively lower external pressure allows pressurized fluid to exit the needle while openings remaining in higher pressure, non-target regions do not release substantial amounts of the fluid.

7 Claims, 19 Drawing Sheets

(51) Int. Cl.
*A61M 5/32* (2006.01)
*A61M 5/46* (2006.01)
*A61M 5/162* (2006.01)
*A61B 90/00* (2016.01)

(52) U.S. Cl.
CPC .......... *A61B 17/3496* (2013.01); *A61B 90/03* (2016.02); *A61M 5/162* (2013.01); *A61M 5/3291* (2013.01); *A61M 5/46* (2013.01); *A61M 2005/1585* (2013.01)

(58) Field of Classification Search
CPC ..... A61M 5/2459; A61M 5/286; A61B 90/03; A61B 17/3401; A61B 17/3468; A61B 17/3496
USPC ........................................................ 604/244
See application file for complete search history.

(56) References Cited

U.S. PATENT DOCUMENTS

| | | | |
|---|---|---|---|
| 4,983,166 A | 1/1991 | Yamawaki | |
| 5,232,442 A | 8/1993 | Johnson et al. | |
| 5,300,084 A | 4/1994 | Johnson | |
| 5,334,159 A | 8/1994 | Turkel | |
| 5,517,846 A | 5/1996 | Caggiani | |
| 5,685,852 A | 11/1997 | Turkel et al. | |
| 5,713,874 A * | 2/1998 | Ferber | A61M 5/32 604/1 |
| 5,797,906 A | 8/1998 | Rhum et al. | |
| 5,836,914 A | 11/1998 | Houghton | |
| 6,001,084 A | 12/1999 | Riek et al. | |
| 6,190,370 B1 | 2/2001 | Tsui | |
| 6,512,958 B1 | 1/2003 | Swoyer et al. | |
| 8,920,388 B2 | 12/2014 | Slocum et al. | |
| 2001/0034503 A1* | 10/2001 | Mehier | A61M 5/44 604/158 |
| 2003/0078562 A1* | 4/2003 | Makower | A61B 17/12109 604/509 |
| 2004/0092893 A1* | 5/2004 | Haider | A61M 5/148 604/272 |
| 2006/0064009 A1 | 3/2006 | Webler et al. | |
| 2006/0173480 A1* | 8/2006 | Zhang | A61B 17/3494 606/185 |
| 2007/0142766 A1 | 6/2007 | Sundar et al. | |
| 2007/0244446 A1 | 10/2007 | Sundar et al. | |
| 2008/0249467 A1 | 10/2008 | Burnett et al. | |
| 2009/0131825 A1 | 5/2009 | Burbank et al. | |
| 2011/0125107 A1* | 5/2011 | Slocum | A61B 17/3401 604/272 |

OTHER PUBLICATIONS

International Preliminary Report on Patentability for PCT/US2013/053955 dated Feb. 26, 2015.
Jedwab et al., A study of the geometrical and mechanical properties of a self-expanding metallic stent—theory and experiment. J Appl Biomater. 1993 Spring;4(1):77-85.

\* cited by examiner

← F

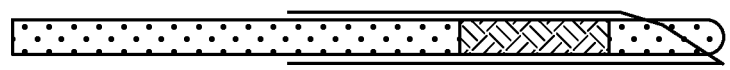
FIG. 7A
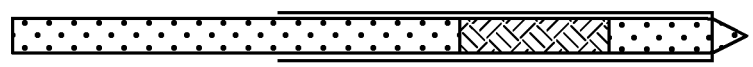
FIG. 7B
FIG. 7C$_i$
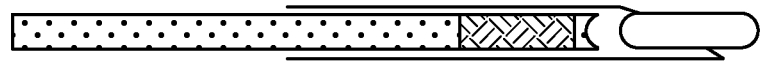
FIG. 7C$_{ii}$

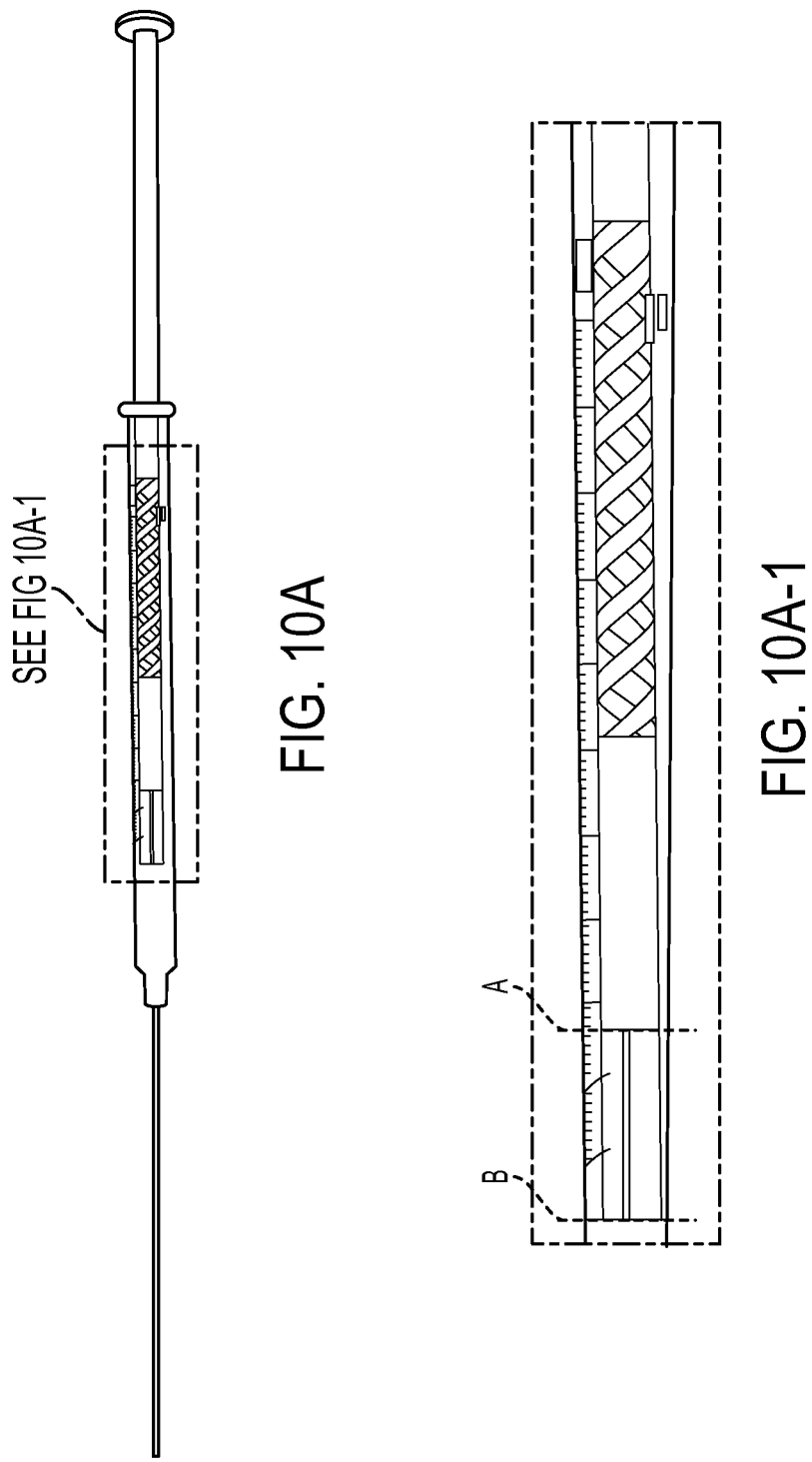

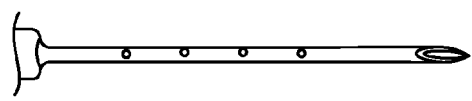
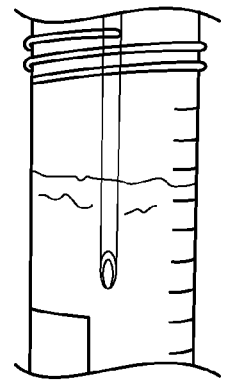
FIG. 14A               FIG. 14B
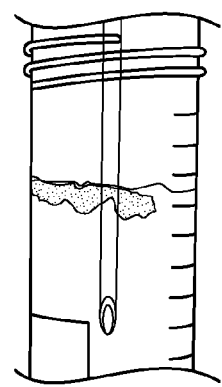
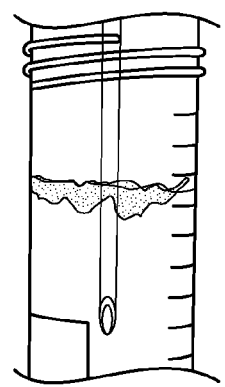
FIG. 14C               FIG. 14D

METHODS AND DEVICES FOR INSERTING A NEEDLE

CROSS-REFERENCE TO RELATED APPLICATIONS

This application is a national stage filing under 35 U.S.C. § 371 of international application PCT/US2013/053955, filed Aug. 7, 2013, which claims the benefit under 35 U.S.C. § 119(e) of U.S. provisional application Ser. No. 61/682,503, filed Aug. 13, 2012, each of which is incorporated by reference herein in its entirety.

FIELD

The inventions disclosed herein relate generally to penetrating medical devices, and more particularly to penetrating medical devices, such as needles, that are to be placed into specific tissues or regions of various tissues or tissue compartments.

DISCUSSION OF RELATED ART

Various medical procedures employ the placement of needles or other penetrating medical devices within the body. Because direct visual observation of the position of the devices within the body is not possible in many procedures, placement of the devices can be challenging. Examples of medical procedures in which placement of a penetrating device is important include:

Arterial Cannulation

Arterial Cannulation (A-lines) is a common procedure in surgery and intensive care to allow arterial pressure monitoring, repeated blood gas sampling, and access to blood for other quantitative assays. Typically, A-lines are inserted in the radial artery of the wrist, but also may be inserted into the axillary artery in the underarm, the femoral artery in the groin, and the pedal artery in the foot. Over eight million A-lines are placed each year in the USA and over 2.5 million are placed in Europe each year. Recently, a 2004 guest editorial in the Journal of Critical Care commented that "even such a frequently used and seemingly benign procedure as cannulation of the radial artery can result in serious complications. The possibility of complications is especially high in critically ill patients who have other co-morbid conditions." Significant complications such as arterial thrombosis, infection, hematoma, nerve injury, and ischemia leading to necrosis of tissues are estimated to range from 15% to 40% and the risk increases with multiple puncture attempts which are often required. In fact, approximately 20% of procedures result in temporary occlusion of the artery requiring an additional puncture event. The increase in risk with multiple punctures is due to direct trauma and increased risk of vasospasm. Multiple punctures also increase the time of the procedure which is typically performed under emergent conditions and thus can compromise stability and life of the patient. Additional attempts typically may be required in as many as 65% of procedures. Inability on the part of the clinician to pass the wire or catheter through the artery is one of the most common difficulties in catheterization. This can occur despite the return of pulsatile blood due to the angle of the needle in relation to the vessel. That is, the angle may be too acute or because the tip is not completely placed within the artery.

Central Venous Catheterization

Central venous catheterization (CVC), or central line placement, involves the cannulation of a vein with a relatively large bore catheter. Central lines are inserted into patients needing access for large amount of fluid administration; those needing monitoring of the central venous pressure; or patients on long-term intravenous therapies for administration of nutrition or medications (i.e., fluids, blood and derivatives, drugs, parenteral nutrition). The most common sites of insertion are the internal jugular vein (neck), subclavian vein (chest), or femoral vein (groin). Central line placement is generally performed by identifying external anatomical landmarks. However, typical anatomical variation of veins is approximately 8% and can be as high as 36% in cancer patients which can complicate CVC. Furthermore, the complication rate may correlate with the physician's level of experience. Therefore, it is not surprising that this procedure is associated with complications such as pneumothorax, inadvertent arterial central line placement, nerve injury, and hematoma in reportedly 14% of patients during emergent procedures.

Aside from requiring multiple needle insertions, occasionally arteries are incorrectly identified as veins and this misidentification is associated with a high incidence of related complications. Specifically, inadvertent placement of a central line into an artery instead of a vein is a prominent cause of morbidity and mortality and may occur in as many as 4.2% of cannulation procedures.

FIG. 1 shows a central line catheter 100 being tunneled under the skin and advanced through the subclavian vein 102 into the right side of the heart.

Epidural Placement

The current state of the art in epidural anesthesia involves the use of an epidural needle (such as a typical Tuohy needle 200) containing a stylet 202 with a blunt end 204, as shown in FIG. 2. The operator performs a blind pass of needle 200 through several tissue layers listed here in order of penetration, some of which are shown in FIG. 3: 1) skin 206, 2) subcutaneous tissue (not shown), 3) supraspinous ligament (not shown), 4) intraspinous ligament 212, and 5) ligamentum flavum 214 to enter the epidural space 215.

Tuohy needle 200 includes a hollow needle that is slightly curved at the distal end 220. During epidural placement, stylet 202, which includes a solid rod with a blunt end, is inserted into the Tuohy needle to prevent tissue from clogging the barrel of the needle. After the needle reaches the epidural space, the stylet is removed and a catheter 222 is inserted into the epidural space via the epidural needle. The curved end of the needle ensures that they catheter is inserted superiorly to the needle within the epidural space. The properly positioned catheter is connected to a syringe 224 for injection of anesthetic agent.

To guide proper placement, the operator uses anatomical landmarks identified by palpation together with changes in the force required to insert the needle through various layers of tissue. Consequently, successful epidural catheter placement requires a high degree of clinical skill on the part of the operator. To ensure proper placement of the needle tip, the operator delicately navigates the needle through the local anatomy, and substantially relies on manual haptic feedback to avoid puncturing the dura 216 and the spinal cord 218 which lies deep to the dura 216. Extreme caution is therefore exercised in the positioning of the needle tip within the narrow epidural space (see epidural space 215 in FIG. 3). To complicate matters, the epidural space has an irregular configuration and therefore the depth of needle penetration depends on the needle trajectory. In addition, during pregnancy and in morbidly obese patients, the anatomical landmarks are typically largely obscured. Attempts to correlate skin-to-epidural space distance with patient variables such as body-to-mass index have not proven useful and thus identification of the epidural space remains a technically demanding procedure, especially given that the skin-to-epidural space distance varies between 20-90 mm. If the needle is inserted too far resulting in the puncture of the dura matter and reaching the subarachnoid space, which occurs in approximately 3% of placement attempts (representing an incidence of 72,000 per year in the U.S. alone), a loss of cerebrospinal fluid (CSF) may ensue leading to disabling complications such as Post-dural Puncture Headache (PDPH) in 50% of these patients. If this misplacement is undetected and the falsely placed epidural catheter is utilized, the anesthesia in the subarachnoid space may reach high enough levels to cause spinal blockade and/or severe motor blockade, which may ultimately result in a rare but devastating complication of respiratory arrest hemodynamic shock.

SUMMARY

Various embodiments disclosed herein may be used for one or more types of medical procedures, including, but not limited to: Vascular Access such as arterial cannulation, central venous catheterization, or AV Fistula Access; lymphatic access; Peritoneal Access; intra-articular injection; intervertebral injection; general catheter placement; administration of epidurals or spinal anesthesia; placement of chest tubes; peritoneal punctures; suprachoroidal injection; ocular injection; Nucleoplasty®; percutaneous access to the brain; and laparoscopy. In some embodiments, the methods and devices disclosed herein may be used to sense tissue location, cavity location, or other locations in the body. Method and devices disclosed herein also may be used to deliver agents of interest in solution or suspension to a body, and/or to collect samples of tissues, cells or fluids. Various embodiments disclosed herein may be used as part of other procedures, including, but not limited to: removal of fluid, tissue, an implanted device, or air; addition of fluid, graft tissue, a device, or air; delivery of adhesives, sutures, staples, graft material, or graft substitute; and detection of cancerous tissue or borders of cancerous tissue. Such procedures may be performed as part of human or veterinarian procedures.

Various embodiments disclosed herein may be particularly useful when performing procedures on obese patients. As only one example, embodiments disclosed herein may be helpful in preventing complications associated with performing laparoscopy on obese patients. Initial needle placement for insufflation of gas into the peritoneal cavity can puncture organs due to the difficulty of sensing entry into the peritoneal cavity.

Infusion of a fluid including a drug, or other fluids is achieved in some embodiments disclosed herein by providing multiple openings along a length of a penetrating medical device. With the fluid within the device pressurized, fluid exits only the opening which is in a region of lower pressure, e.g., a target site for infusion of fluid.

In some embodiments, placement of a penetrating medical device during a medical procedure is achieved by incorporating a braided component into a lumen of the medical device that responds to pressure encountered at the tip of the device. The component may be used to sense position and/or as part of a system of controlling advancement of the medical device.

According to one aspect of embodiments of the invention disclosed herein, an apparatus is provided that can respond to changes in pressure, force, or other parameter such that when the apparatus reaches matter of a certain resistance, the apparatus responds. The response may be used to indicate, such as to a human operator or a machine controller, the position of the tip and/or an opening in the apparatus.

According to one embodiment, a medical device which is adapted to penetrate a body includes a first element having a distal tip and a lumen having an opening, and a force-providing element disposed in the lumen. The force-providing element includes a braided member, the braided member being configured to receive an applied force and selectively transfer at least a portion of the applied force to the first element based at least in part on the resistance of the matter which the force-providing element contacts at the opening.

According to another embodiment, a method of positioning a penetrating medical device within a body is provided. The device includes a first element having a distal tip and a second element, the second element comprising a braided portion and a distal surface adjacent the distal tip of the first element. The method includes inserting the distal tip into the body with the surface in contact with the body, exerting a force on the second element, the force expanding the braided portion when the distal tip of the penetrating medical device is positioned in a first region having a first resistance to advancement such that the braided portion expands to contact an internal surface of the first element and frictionally transfers at least a portion of the force to the first element. By this action, a driving force is applied to the first element to advance the penetrating medical device through the body. The method further includes exerting a force on the second element while the distal tip of the penetrating medical device is positioned in a second region having a second resistance to advancement of the penetrating medical device through the body, the braided portion contracting such that any amount of force frictionally transferred from the second element to the first element is insufficient to advance the penetrating medical device through the body. Also included in the method is moving the second element longitudinally relative to the first element when the distal tip of the penetrating medical device is positioned in the second region.

According to a further embodiment, a method of infusing a fluid includes providing a penetrating element having a lumen and a plurality of lumen openings spaced longitudinally along a sidewall of the penetrating element lumen, and penetrating the penetrating element into a body to a position at which at least one of the lumen openings is positioned in a target region. The method further includes providing fluid to the lumen, pressurizing the fluid in the lumen to a first pressure which forces the fluid to exit the lumen through the at least one of the lumen openings that is positioned in the target region, and the first pressure is insufficient to force the fluid to substantially exit the one or more lumen openings that are not positioned in the target region.

According to yet another embodiment, a medical device for placing at least one lumen opening in a target region within a body is provided. The device includes a penetrating element having a penetrating distal tip, a lumen, and a plurality of lumen openings spaced longitudinally along the lumen and in a sidewall of the penetrating element.

According to a further embodiment, a medical device for placing at least one lumen opening in a target region within a body is provided. The device includes a penetrating element having a penetrating distal tip, a distal region, a lumen, and a plurality of lumen openings spaced longitudinally along the distal region of the penetrating element.

In another embodiment, a medical device for placing at least one lumen opening in a target region within a body includes a penetrating device having a first lumen and a first lumen opening, a membrane configured to inflate at the lumen opening when fluid within the lumen is pressurized, and a second lumen opening through which fluid can be selectively infused into a target region in a body.

According to a further embodiment, a device adapted to penetrate a body includes at least one first member having a distal tip and a lumen having an opening on a sidewall of the first member, and a second member disposed within the lumen. The second member has a structural surface exposed through the opening, and the second member is adapted to have a first state in response to a first pressure on the surface and a second state in response to a second pressure on the surface.

According to yet another embodiment, a medical device is adapted to penetrate a body, and the device includes a first element having a distal tip and a lumen having an opening. The device also includes a force-providing element disposed in the lumen. The force-providing element includes a plurality of long and thin flexible elements, the member being configured to receive an applied force and selectively transfer at least a portion of the applied force to the first element based at least in part on the resistance of the matter which the force-providing element contacts at the opening.

All aspects of the invention need not be present in various embodiments of the invention, and one embodiment may instantiate multiple aspects. Various combinations of aspects and features disclosed herein may be present in embodiments of the invention. Additionally, while certain advantages and features of embodiments are described herein, a device, apparatus, system or method need not necessarily provide every advantage or include every feature to fall within the scope of the invention.

BRIEF DESCRIPTION OF THE DRAWINGS

FIG. 5b, shows one embodiment of a braided clutch mechanism on the stylet body located inside the needle of FIG. 5a;

FIG. 7a shows one embodiment of a clutch system;

FIG. 7b shows one embodiment of a clutch system where a cutting element is provide on a stylet instead of an outer tube, and the clutch element is constructed and arranged to have a poor ability to translate longitudinal force once the clutch element has exited the outer tube;

Figure 1:
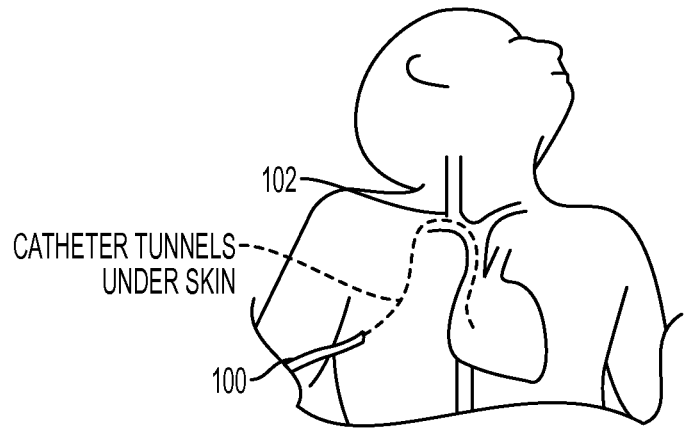
FIG. 1 shows a prior art method of central venous catheter placement within the subclavian vein and into the right side of the heart.
Figure 2:
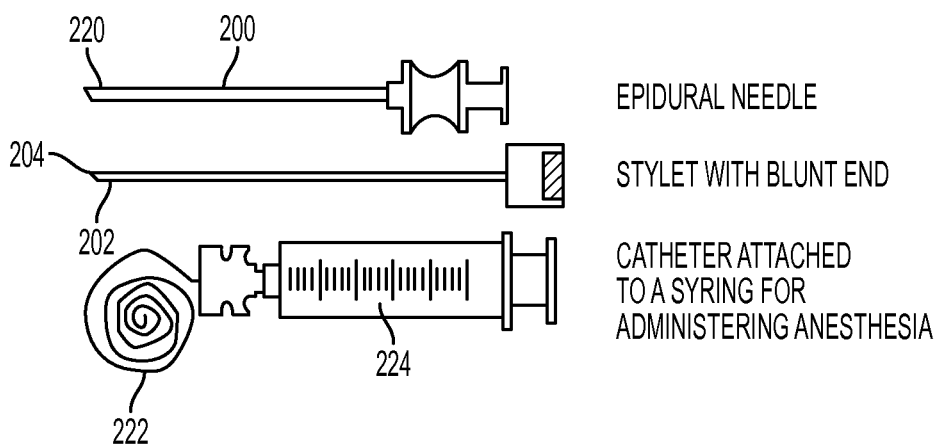
FIG. 2 shows a prior art Tuohy needle and associated components.
Figure 3:
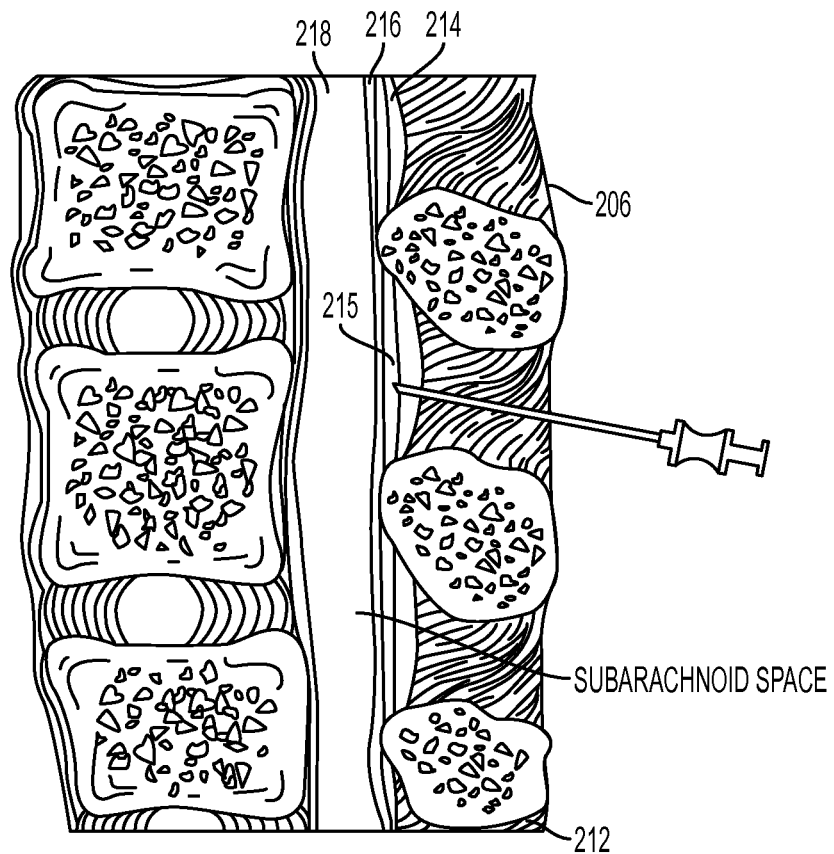
FIG. 3 shows a prior art Tuohy needle being advanced into the epidural space.
Figure 8A:
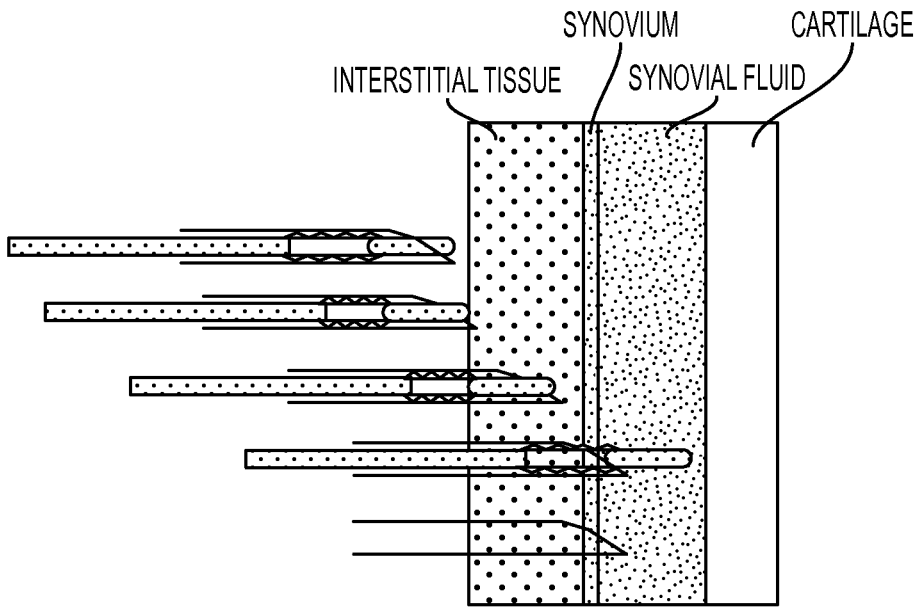
Figure 8B:
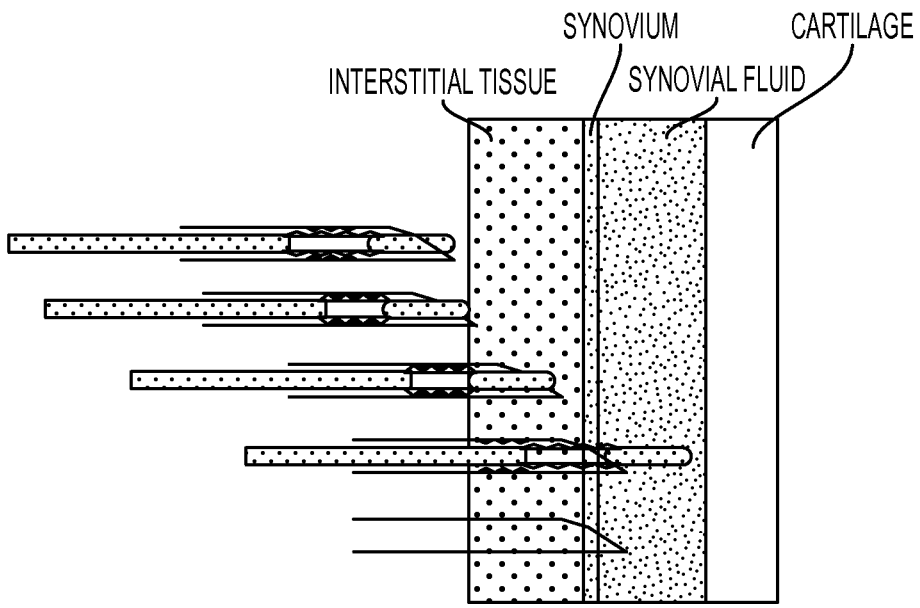
Figure 9:
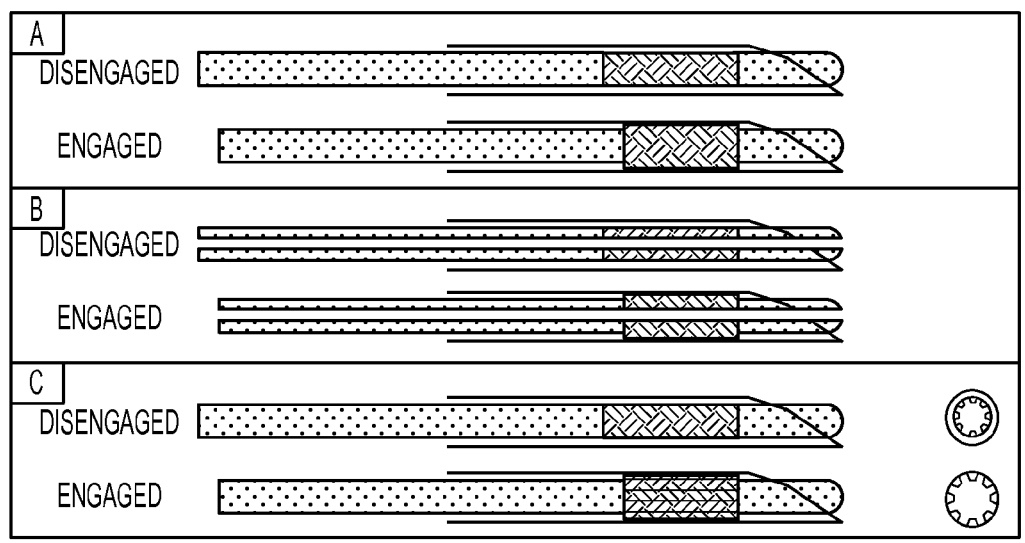

FIGS. $7c_i$ and $7c_{ii}$ show one embodiment of a clutch system configured to push a capsule which is free to detach once a cavity is reached;

FIG. 8a illustrates a bellows-based clutch mechanism;

FIG. 8b illustrates a bellows-based clutch mechanism with corresponding engaging feature on the inner diameter of the needle;

FIG. 9a shows one embodiment of a clutch mechanism with a poisson clutch mechanism;

FIG. 9b shows one embodiment of a clutch mechanism including a central bore to allow the flow of fluid through a lumen of the needle;

FIG. 9c shows one embodiment of a clutch mechanism having a finned structure on the outside of the clutch which facilitates engagement of the clutch while allowing fluid to pass through the needle;

FIG. 10a shows one embodiment of an external clutch system;

FIG. 10a-1 is an enlarged partial view of FIG. 10a.

Figure 10B:
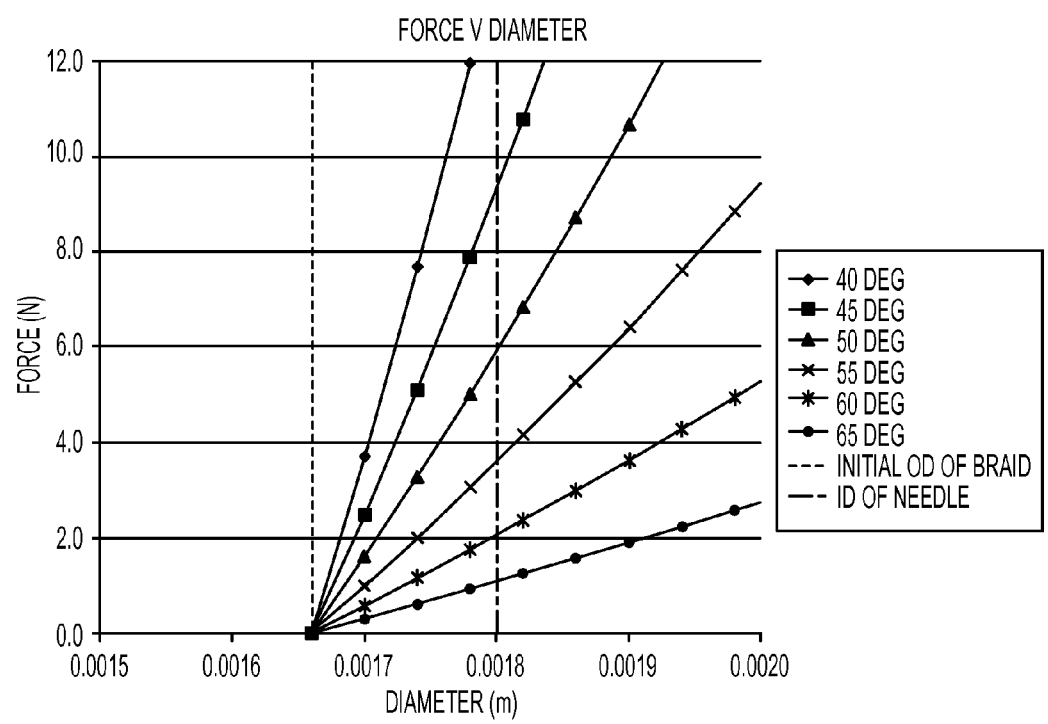
Figure 11:
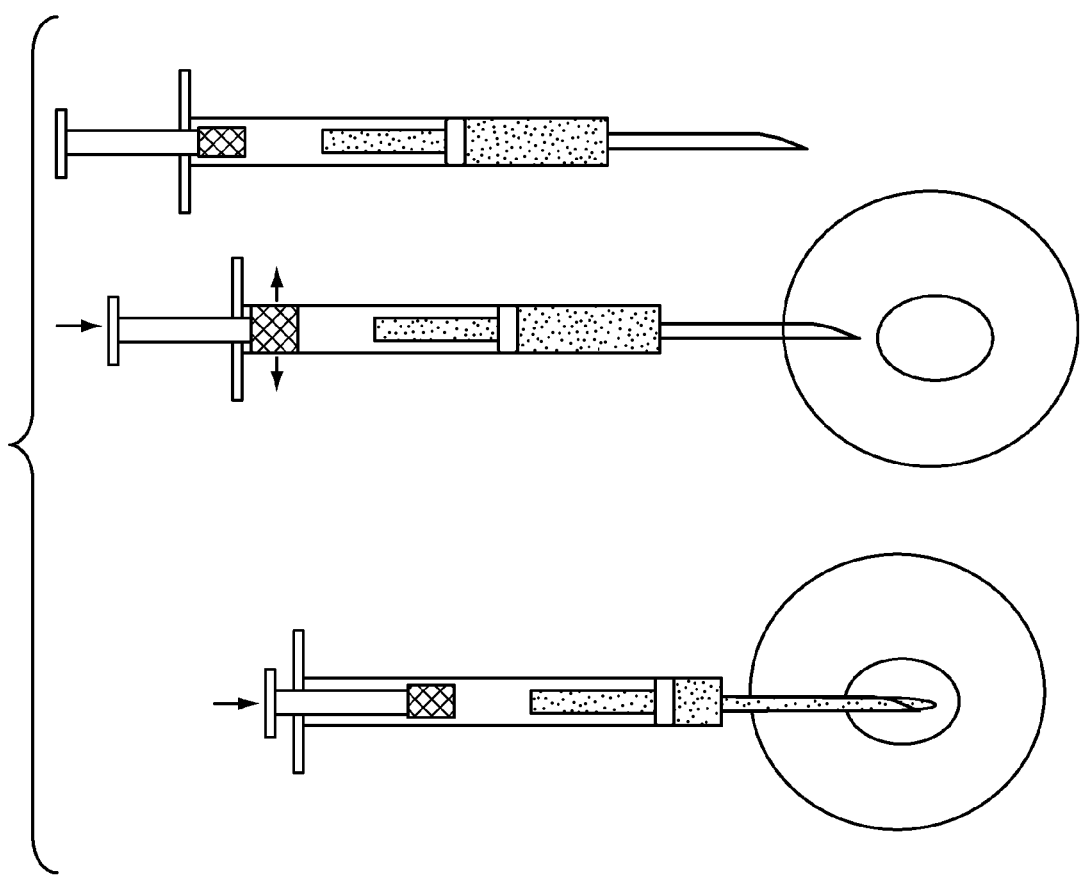
Figure 12A:
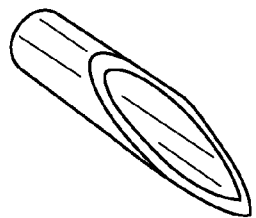
Figure 12B:
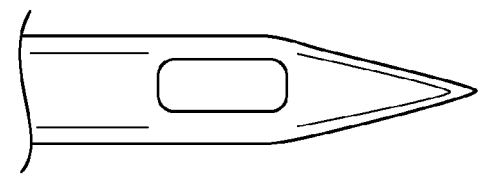
Figure 13A:
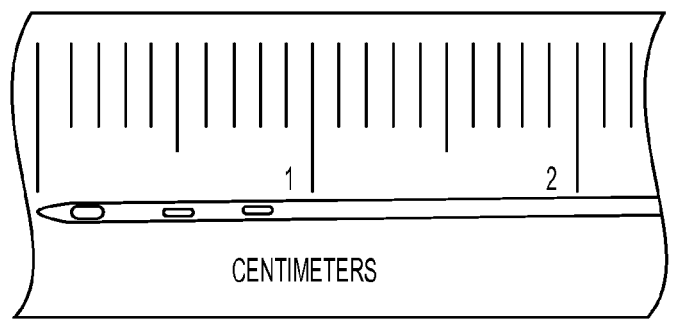
Figure 13B:
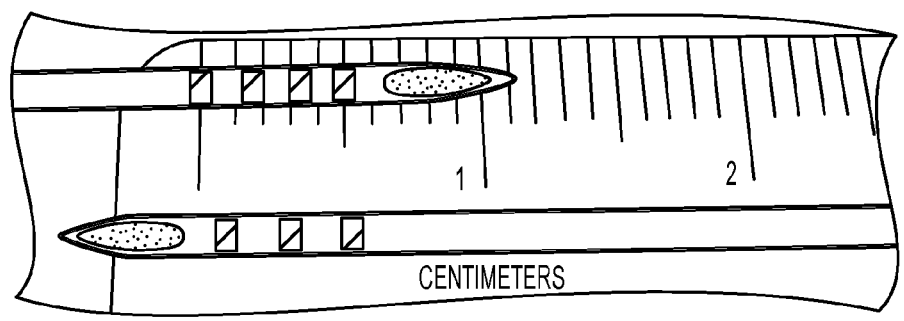
Figure 15:
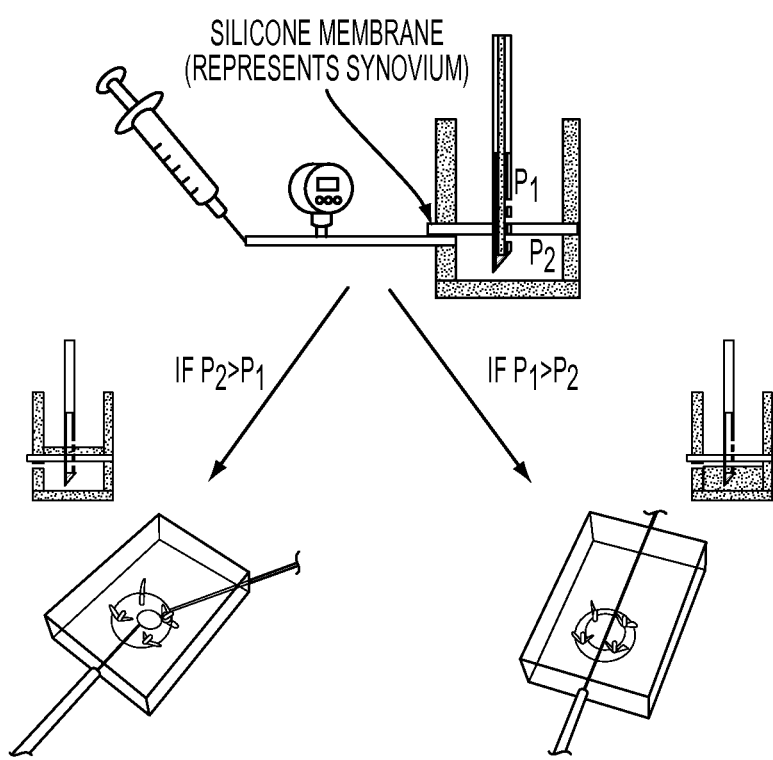
Figure 16:
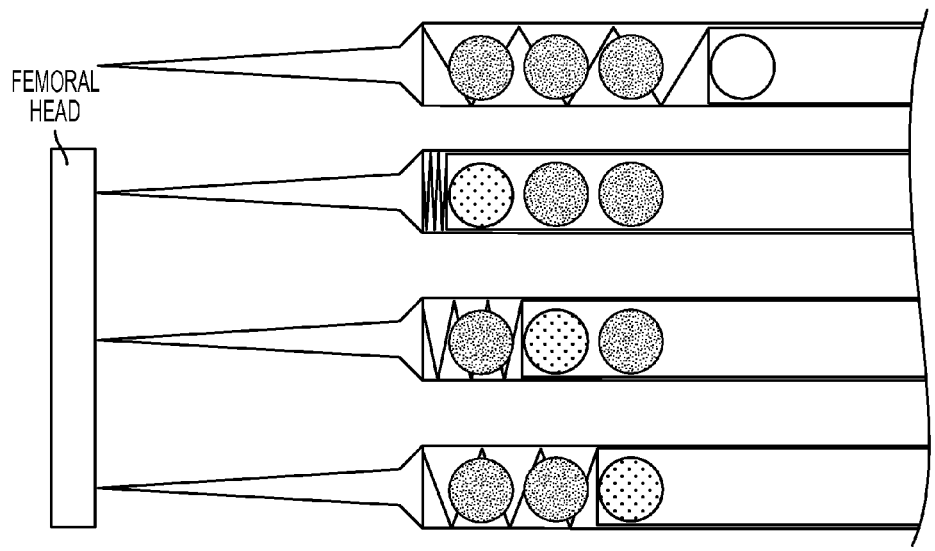
Figure 17:
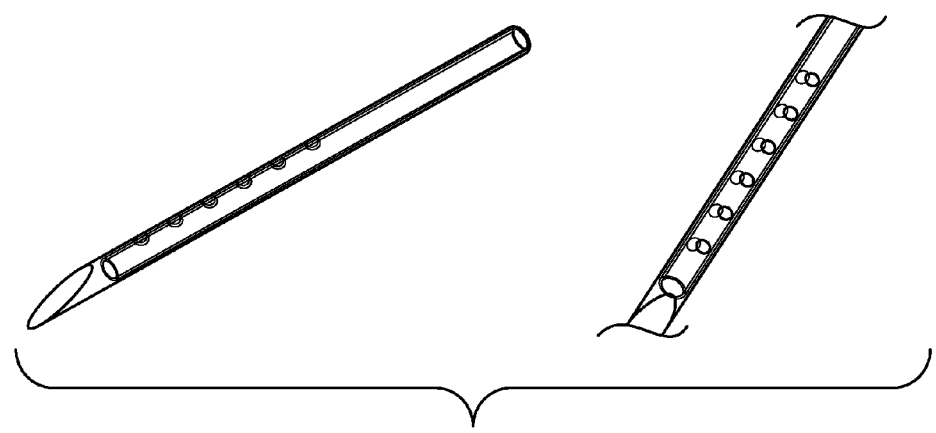
Figure 18:
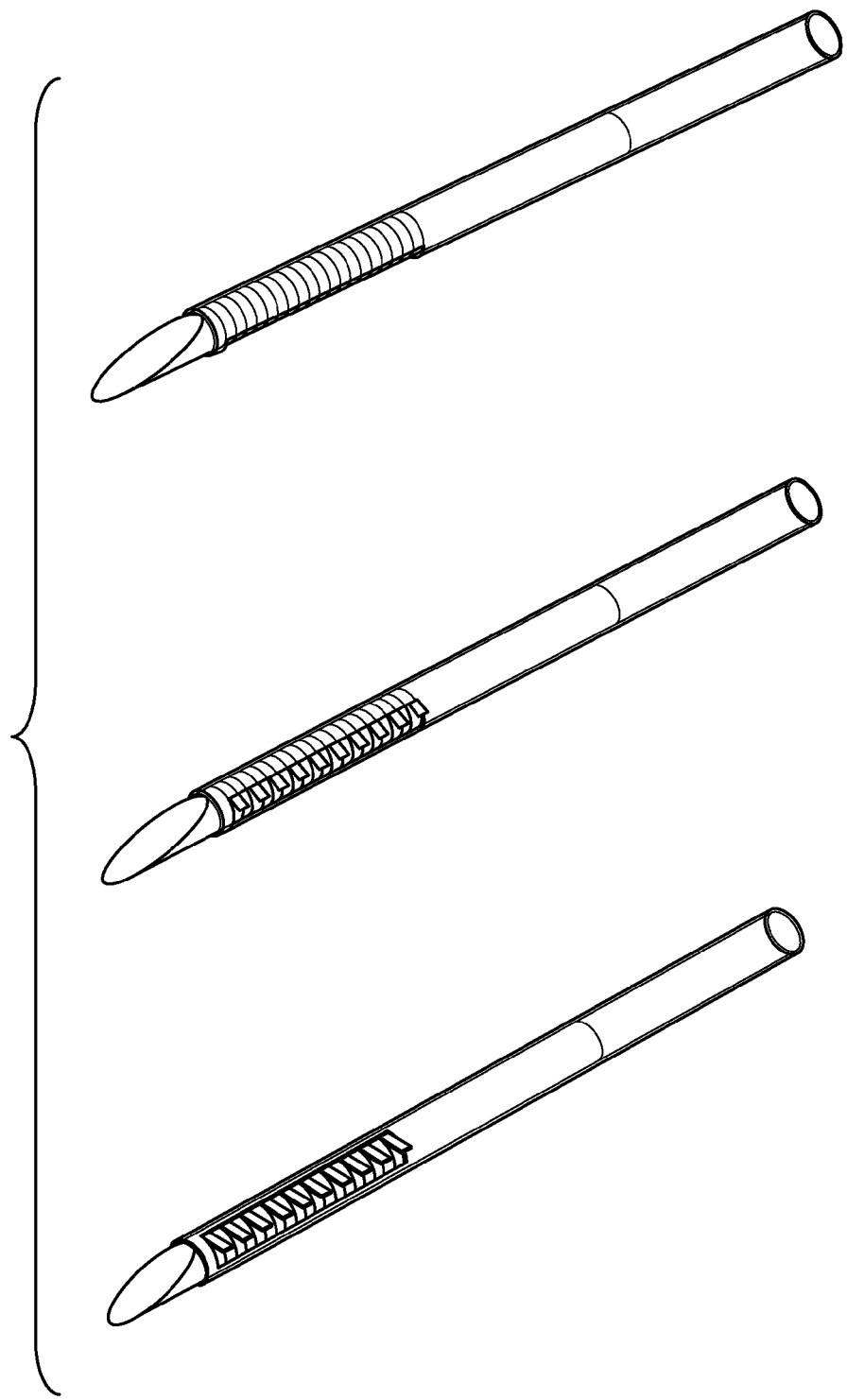
Figure 19:
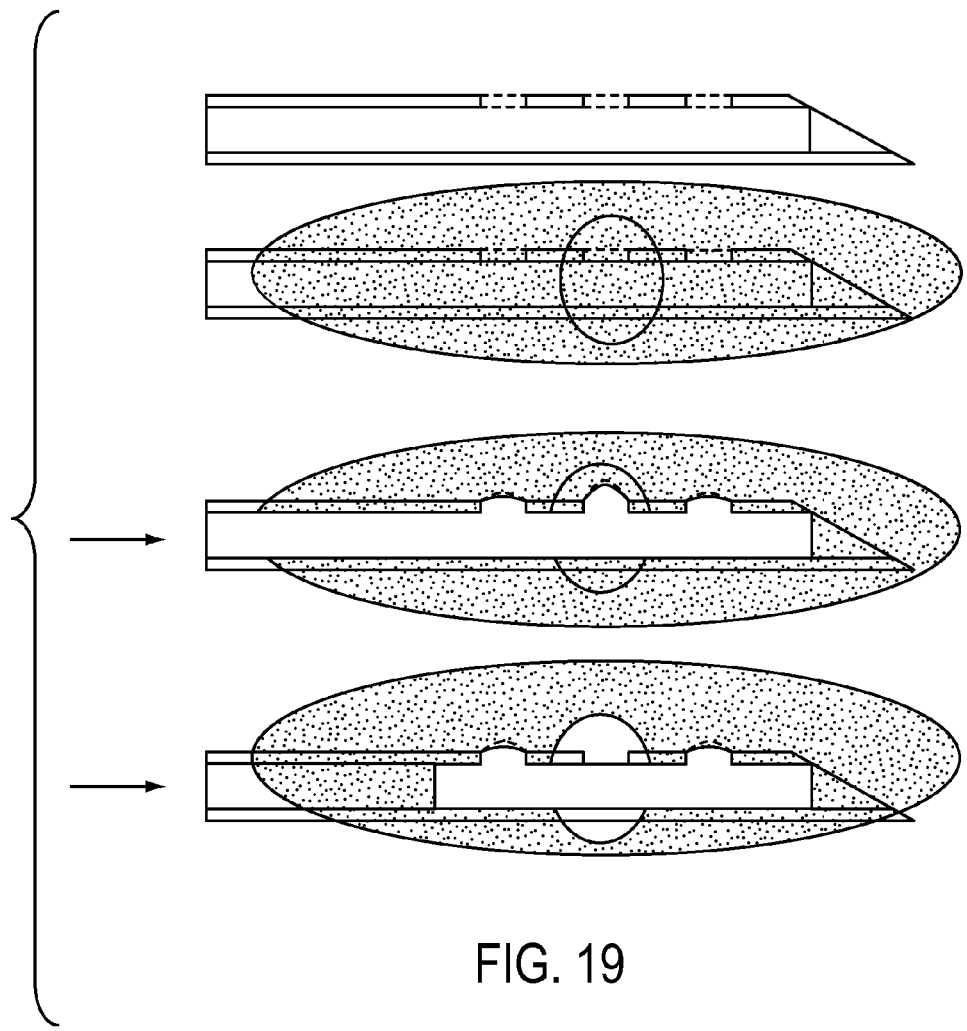
Figure 20:
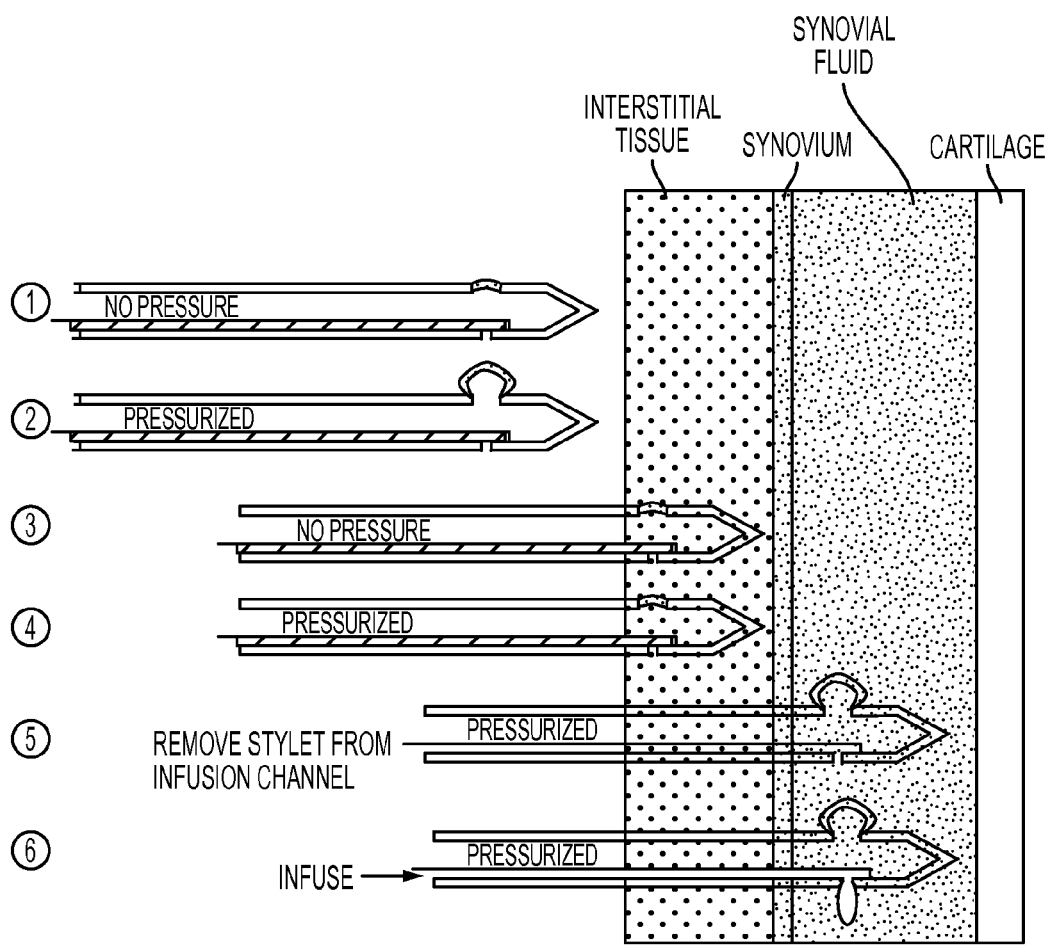
Figure 21:
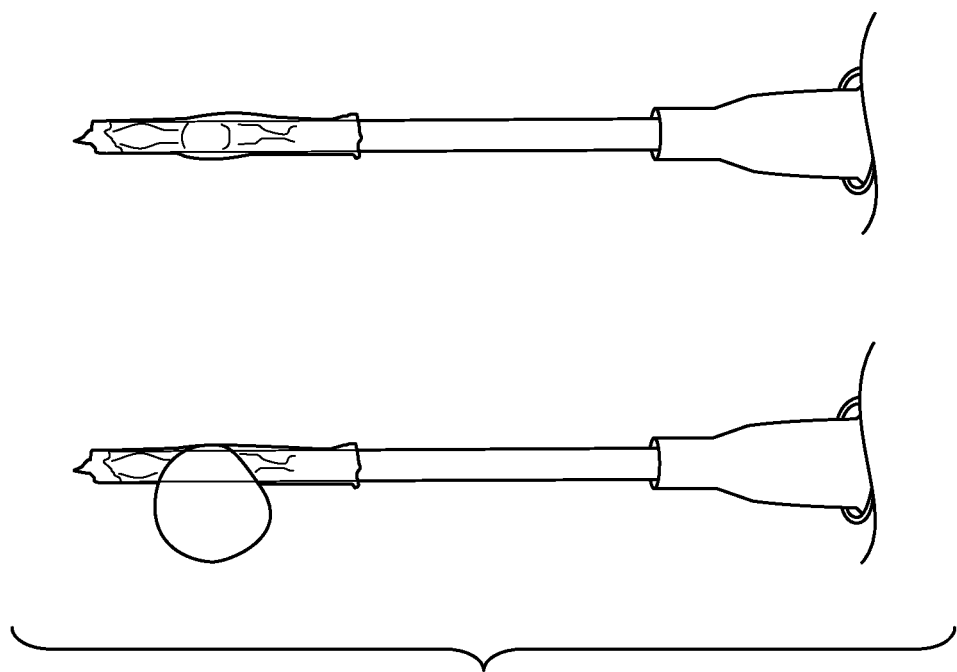

FIG. 10b shows a graph of results from an analytical model of an expanding metallic stent;

FIG. 11 shows one embodiment of a syringe incorporating a clutch mechanism;

FIG. 12a shows a typical double bevel needle;

FIG. 12b illustrates a pencil point needle, with a centrally located cutting point and recessed eye;

FIG. 13a shows a modified 22 Ga multi-hole needle with three rectangular slots, each 1 mm long, according to one embodiment;

FIG. 13b shows modified 18 Ga needles plugged at their distal tips with epoxy;

FIGS. 14a-14d show selective infusion using a multi-hole needle to the site of least resistance;

FIG. 15 illustrates one embodiment of pressure dependent selective infusion using a multi-hole needle in a bench top model. Pressure inside the chamber (P2) can be varied by adjusting the attached syringe;

FIG. 16 shows one embodiment of a multi-hole Sprotte stylet needle with an internal tube having a single orifice, which can be retracted in a corkscrew-like, helical or spring-loaded fashion such that once a drop in resistance is felt, the physician can inject into the region of least resistance;

FIG. 17 shows one embodiment of a multi-hole needle, where the positioning of an orifice in the inner element relative to the outer needle controls the pressure required to infuse the drug through the needle;

FIG. 18 shows one embodiment of a tunable multi-hole needle with cantilever style elements covering the holes in the inner element through which a drug may be infused;

FIG. 19 illustrates one embodiment of a multi-hole needle with a breakable membrane such as a coating or a balloon. In this case, the balloon covering the hole in the pocket of least resistance (the middle balloon) expands before the other balloons. The balloon fractures, through mechanical failure or by contacting a sharp element as it exists the orifice. Once a single hole is opened, the pressure on the other balloons is reduced. The drug is infused at a slow rate to ensure no other balloons are ruptured;

FIG. 20 shows one embodiment of a dual lumen balloon anchor infusion device shown anchoring and infusing in the synovial sac; and FIG. 21 shows one embodiment of a pressure sensitive, thin-walled balloon for cavity sensing and for providing tactile feedback to the user regarding correct positioning.

DETAILED DESCRIPTION

In some embodiments, resistance encountered at the tip of a device may be used to control a clutch mechanism to create an apparatus that provides a driving force to a penetrating medical device when the apparatus tip encounters material of high resistance, and when the apparatus tip encounters a low resistance material, no further driving force (or a significantly reduced driving force) is applied to the apparatus. Such an apparatus may be used to stop or slow advancement the tip of a device upon reaching a desired low resistance area, regardless of whether the operator continues to apply force to certain components.

1. Clutch Mechanism Overview

Figure 4:
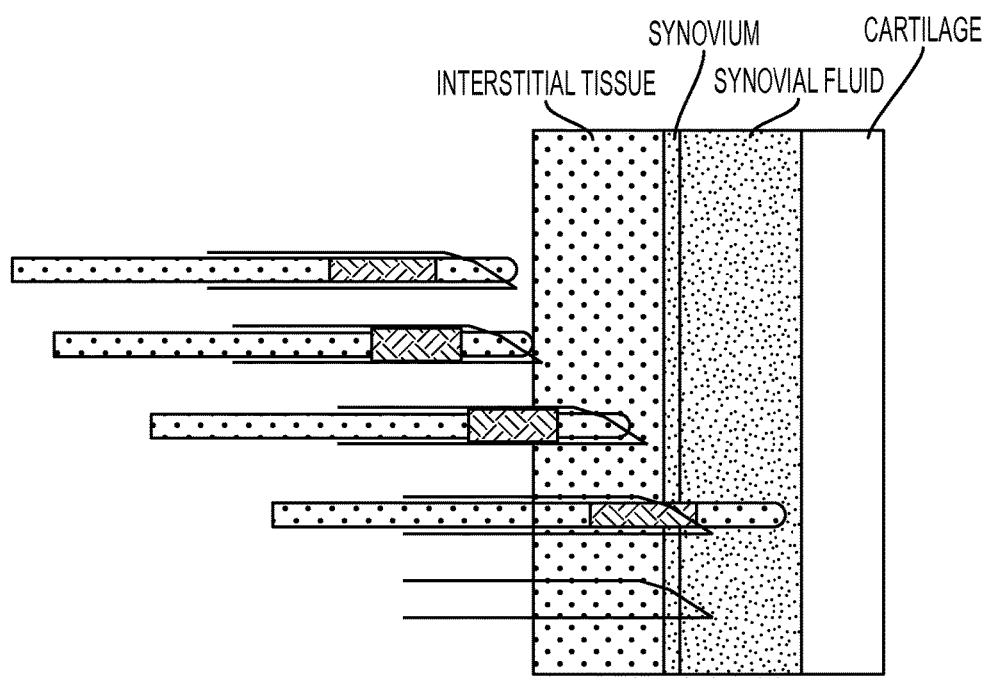
FIG. 4 shows one embodiment of a clutch mechanism being used to access a synovial sac.
Figure 5A:
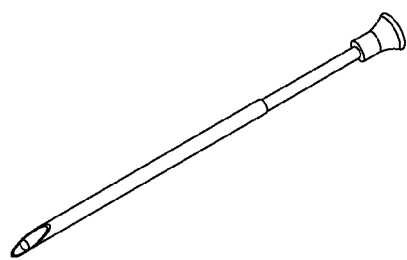
FIG. 5a shows one embodiment of a needle with a stylet in place.
Figure 5B:
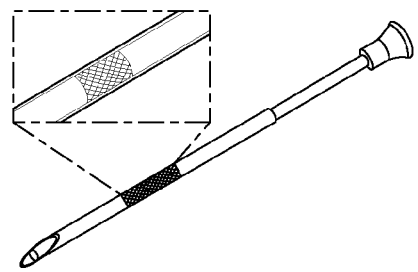
Figure 5C:
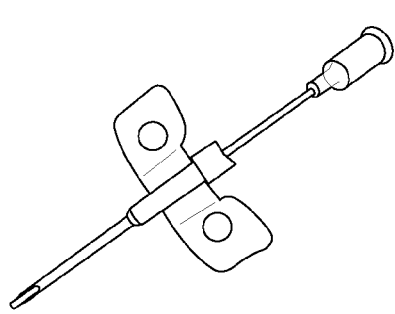
FIG. 5c shows one embodiment of a stylet with the braided clutch mechanism of FIG. 5b placed inside a 14 Ga dialysis needle.
Figure 5D:
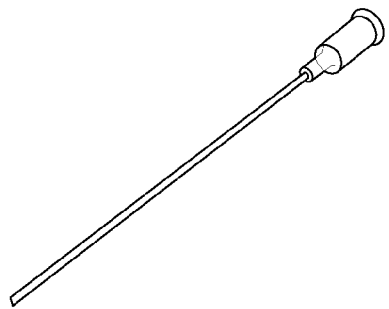
FIG. 5d shows one embodiment of a stylet which may include a braided clutch mechanism, the braid including sixteen 0.002"×0.005" flat 304 stainless steel wires.

FIG. 4 provides an overview of the principle of placing the needle in a target site (in this case the synovial sac) using a clutch-based mechanism. This method relies on an increase in mechanical resistance (RSYM) as the combined needle and stylet cross from a first compartment or region to a second component or region. For example, in some embodiments, the combined needle and stylet may be moved through the synovium into the synovial fluid (RSF). Various embodiments are described below.

Of course devices and methods described herein may be used at other target sites or regions, such as other within other types of tissues.

1.1 Braid Mechanism

FIGS. 5a-5d illustrate one embodiment of a needle arrangement incorporating a clutch mechanism. The clutch mechanism on the stylet body includes an expandable and contractible member which is made of a plurality of flexible elements, such as long, thin wires. In some embodiments, the flexible elements may be interlaced. For example, in some embodiments, a series of flat wires are interlaced to form a braid. The flat wires may be the type typically used to form the body of catheters and wire-based stents such as the Wallstent. This braided shaft forms part of the inner core insert or stylet. When axially loading is applied to the inner core, the braided shaft component undergoes a change in its architecture wherein it expands from a first diameter to a larger, second diameter. The braided shaft can be configured such that the larger, second diameter exceeds the inner diameter of the tube or needle component (outer element). This expansion causes the braided shaft to engage with the outer element until the axial load is reduced on the inner core. Unlike a conventional coil, the braid expands radially in an efficient and repeatable manner when axially loaded. In some embodiments, this arrangement relies predominately on elastic behavior rather than a buckling mode, which may induce plastic deformation. This approach of using elastic behavior reduces the variability within the system, allowing for a smooth transition between engagement and disengagement of the clutch. The braid expands uniformly, simultaneously inducing multiple points of contact with the inside of the needle. The sensitivity of the mechanism can be adjusted by varying one or more of 1) the pics per inch (PPI) of the braid and hence the braid angle, 2) the cross sectional profile of the wires and 3) the gap between the outer diameter of the relaxed braid and the inner diameter of the needle 4) the composition of the braid, and 5) the composition of the material with which the braid engages.

The braid PPI may by any suitable PPI between 10-70 PPI inclusive in some embodiments, or any suitable PPI between 30-50 PPI inclusive in some embodiments. Cross-sectional profiles may be circular, elliptical, square, rectangular, or any other suitable shape. In some embodiments, the gap between the outer diameter of the relaxed braid and the inner diameter of the needle is sufficient to ensure that there is limited frictional contact between the braid and the needle when the braid is in its relaxed state. In some embodiments of smaller diameter applications, the gap may be 1 mm or less.

The braid is typically made of one or more metals, such as stainless steel, nitinol, cobalt chromium, or polymers, or a combination thereof, or any other suitable metal or material. The material and surface topography of the needle may include a metallic or polymeric coating.

In some embodiments, the long, thin flexible wires or other elements may not be interlaced, but instead be grouped together. For example, several, dozens, or hundreds of long, thin, flexible wires may be bundled together to form a clutch mechanism. The wires may bow outwardly when a force is applied to an end of the group of wires.

Figure 6A:
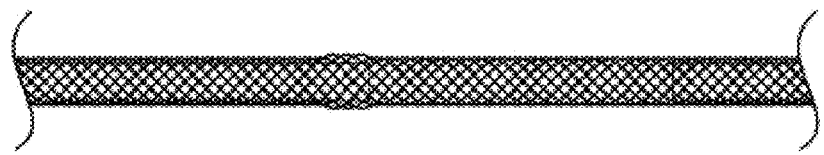
FIG. 6a shows one embodiment of a stylet with a braided clutch mechanism in a relaxed state such that the stylet is free to move inside a sheath.
Figure 6B:
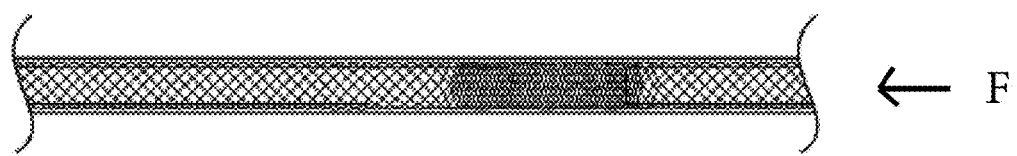
FIG. 6b shows a longitudinal force F being applied to the stylet of FIG. 6a, causing the clutch to engage with the sheath.
Figure 6C:
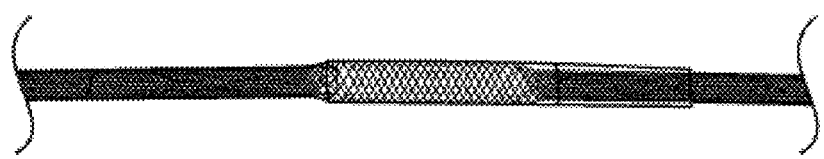
FIG. 6c shows one embodiment of braided clutch mechanism which permits fluid to pass through a lumen of a stylet.
Figure 6D:
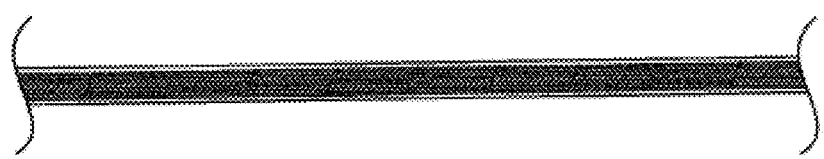
FIG. 6d shows another embodiment wherein the needle and stylet may be placed over a guidewire.

Further advantages of this new approach are shown in FIGS. 6c and 6d. Because the braid mechanism is placed on a tubular stylet with a lumen in some embodiments, fluid can pass freely through the device via the lumen. This arrangement can permit the device to incorporate a "flash back" element for the user, where blood or other internally pressurized fluid can be viewed through a transparent portion toward the proximal end of the needle or syringe (often at the needle hub), providing additional assurance that the correct cavity has been located or reached. Also, the braid based stylet and needle can be placed over a guidewire. This makes the technology usable for a broad range of internal "over-the-wire" catheter-based applications.

Further embodiments of needle system with a clutch mechanism are shown in FIG. 7. In the schematic shown in FIG. 7b, the stylet plays an active role in penetrating through the tissue, while the outer tube is a hollow cannula. The clutch element is designed to buckle easily once it exits the needle, meaning clutch element no longer transmits a longitudinal force to the needle tip. For improved effectiveness, the clutch element is located as close as possible to the distal end of the assembly.

As shown in FIGS. $7C_i$ and $7C_{ii}$, the assembly is designed to deliver a capsule to the cavity in an efficient and user-friendly manner. The capsule is placed at the proximal end of the stylet and slots into a groove but is not attached. When a region of less resistance is reached, the capsule is released in a semi-automated fashion. In certain applications, this could have the advantage of drug delivery with zero or limited blood loss. For purposes herein, the term "capsule" is intended to include pills, tablet, caplets or any other drug delivery device.

1.2 Bellows-Based Clutch

In an alternative embodiment, the clutch mechanism is activated using a bellows arrangement which expands radially under axial compression (see FIG. 8a). The mechanical properties of the bellows and the dimensions of bellows can be tailored to adjust the sensitivity of the clutch mechanism. In FIG. 8b, the bellows mechanism is illustrated with corresponding engagement features on the inner diameter of the needle. The engagement features may provide a positive engagement with the expanded bellows.

1.3 Polymer/Foam Based Clutch

FIG. 9a shows a clutch arrangement with a poisson effect clutch element as described in U.S. Patent Application Publication No. 2011/0125107, which is hereby incorporated by reference. This mechanism is based on the inclusion of a polymer (e.g. a molded foam), which expands radially as it is compressed axially to engage with the needle. FIGS. 9b-9c illustrate various improvements to the arrangement illustrated in FIG. 9a. In FIG. 9b, the clutch element includes a central bore to permit flow of fluid through the needle lumen. The inclusion of this feature facilitates communication between the distal and proximal ends of the needle, which allows for the use of a visual indicator of correct needle placement (e.g., flash back), and/or administration of a drug or other therapeutic agent without the requirement of stylet removal.

A preferred embodiment of this mechanism is illustrated in FIG. 9c, where fin features on the outer diameter of the clutch increase the channel size for fluid flow when the clutch is engaged. To increase the friction between the stylet and the needle in the engaged state, micropatterned bumps (e.g., rubber) or other textures may be included on the outside of the fins.

1.4 External Mechanism

In FIG. 10a, one element of a clutch mechanism is illustrated where the clutch is external to from the needle. This approach has several advantages:

The user is able to view the clutch engaging and disengaging, and also view in some embodiments "flash back" indication from fluid in the target cavity;

The user is familiar with the components used, that is, the device appears similar to a typical syringe;

Modular devices can be used and interchanged easily for adaptability to any current needle product; and Can be used with much smaller needle gauges Further, an indicator may be included so that the user does not push too far. For example, Point A cannot be advanced as far as Point B, otherwise the needle and stylet will advance together (it should be noted that the distance between A and B can be longer or shorter than illustrated in FIG. 7.

The increased working length may induce more variability within the system in some embodiments. The stylet being introduced is very stiff in some embodiments to prevent the stylet distal of the clutch from bending or buckling.

FIG. 10b is a graph showing the results of an analytical model based on Equation 12 from Jedwab and Clerc, "A Study of the Geometrical and Mechanical Properties of a Self-Expanding Metallic Stent—Theory and Experiment", Journal of Applied Biomaterials, Vol. 4, 77-85 (1993), showing the load F acting on a stent. Also see the associated Erratum in Vol. 5, 273 (1994). Equation 12 is provided as:

$$F = 2n\left[\frac{GI_p}{K_3}\left(\frac{2\sin\beta}{K_3} - K_1\right) - \frac{EI\tan\beta}{K_3}\left(\frac{2\cos\beta}{K_3} - K_2\right)\right]$$

where $K_1$, $K_2$ and $K_3$ are constants given by $$K_1 = \frac{\sin 2\beta_0}{D_0}$$

$$K_2 = \frac{2\cos^2\beta_0}{D_0}$$

$$K_3 = \frac{D_0}{\cos\beta_0},$$

I and $I_p$ are the moment of inertia and polar moment of inertiat of the wire, respectively, E is Young's moudulas of elasticity, and G is the rigidity modulus.

The graph in FIG. 10b shows estimates of how the diameter of a radially unconfined braided member changes in response to an axial force. Curves for different initial pitch angles are provided. The analytical model does not incorporate friction or account for contact with a needle.

1.5 Clutch Syringe

FIG. 11 illustrates another embodiment, where the clutch is incorporated into a "loss of resistance" syringe. In this embodiment, a clutch needle or a regular needle is used to locate the target area of reduced resistance. As a means of ensuring that a therapeutic will be delivered only to the target zone, the sensitivity of the clutch is designed such that when the needle tip is located in the high resistance zone, R1, the clutch engages upon attempted depression of the plunger. The plunger mounted clutch engages with the inner diameter of the syringe barrel, causing increased resistance. This increased resistance makes it impossible or extremely difficult to depress the plunger when the needle tip is in R1, providing a safety mechanism for the user. Conversely, when the syringe is located in R2, the resistance at the needle tip is insufficient to cause the clutch to engage with the ID of the syringe barrel, allowing infusion to occur. The clutch mechanism could be located along the length of the barrel, preferably toward the distal end, or it may be incorporated into the plunger tip itself in some embodiments.

For one or more of the embodiments described above, a device that is advanced to a target region may be used to withdraw and/or infuse fluids, such as liquids.

2. Needles that Target and Infuse Selectively

Introduction

While advancements in visualization techniques, such as MRI and ultrasound have facilitated the interventionalist in needle directing, the mechanics of needle insertion and delivery in routine procedures have not changed. There is a need for low cost, user-friendly methods of targeted infusion.

Particular difficulties are encountered when targeted injection is critical to clinical outcome. For example, intra-articular injection with the requirement of drug delivery exclusively to the synovial sac only can pose specific challenges. Conventionally, the physician is unable to routinely detect sufficient tactile feedback when the needle passes through the synovium (a <0.1 mm thick membrane). Applicant has recognized a need for devices which can successfully deliver drugs exclusively to synovial sac, through improved targeting by taking advantage of distinct changes in the local mechanical environment inside the synovial sac compared to the surrounding tissue and/or by providing augmented tactile feedback to the physician. It would be extremely useful for routine outpatient procedures, for the physician to be able to inject with confidence of accurate placement without the requirement for ambiguous, costly and time consuming image guidance.

The methods and devices described herein also may be used for medical procedures including, but not limited to, Vascular Access (including arterial cannulation, central venous catheterization and AV Fistula Access), lymphatic access, Peritoneal Access, Tracheostomy, Placement of chest tubes, Intra-articular Injection, Intervertebral Injection, Epidural and Spinal Anesthesia, Suprachoroidal injection, Ocular Injection, laparoscopy, percutaneous access to the brain, enhanced local delivery of therapeutics to localized tumors. Methods and devices also may be used purely for sensing application, and/or to deliver agents of interest in solution or suspension and/or sample tissues, cells, or fluids. Further applications include access, withdrawal and infusion to and from the bladder, pleural effusion, tympanic membrane, trachea, cricothyroid membrane, embryonic sac, uterus, ventricular drainage, catheter mounted endovascular procedures including crossing a thrombus or emboli, calcification or recannulization.

2.1 Infusion/Aspiration

In the case of targeted infusion to the synovial sac, one approach takes advantage of the pressure differential that exists as the synovium is crossed. Miniaturized pressure transducers are too expensive for use in routine procedures. A 1 mm pressure sensor can sell for approximately $3500 and requires a power line and amplifier which can cost approximately $7000. Applicant has recognized a need for cost-effective devices and methods for selective injection into a target site, such as the synovial sac.

Each of needle design, hole positioning, number of infusing holes and infusion pressure can influence the likelihood of successful delivery. Below, several embodiments which achieve targeted delivery are described, using the example of synovial sac as the target site.

2.1.1 Multi-Hole Needles

Traditionally, standard double bevel needles (see FIG. 12a) have been used for intra-articular aspiration and drug delivery. Applicant has recognized that a design which more closely resembles a Sprotte needle, traditionally used for catheter delivery in intrathecal injections for spinal anesthesia, can achieve more efficient delivery of drug to compartments or potential spaces, such as the synovial sac. In particular, a pencil point needle with multiple openings can be effective. An illustration of a pencil point needle, with a centrally located cutting point and recessed eye is illustrated in FIG. 12b.

2.1.1.1 Multi-hole Needle Pencil Point Needle

One method of improving the likelihood of successful infusion is to use a multi-hole needle approach. Cartilage in the knee joint is usually 1-3 mm thick. The underlying bone can be used as a reference point, such that holes start at 1 mm proximal to the distal tip of the needle. When a fluid filled multi-hole needle is inserted until contact is made with the bone, one or more of the holes is located inside the synovial sac. A collapsed, non-effusive synovial sac tends to have a lower pressure than the surrounding interstitial tissue. When care is taken to infuse at a slow rate, the drug is largely delivered through the holes that offer the least resistance to flow residing in the synovial sac. FIGS. 13A and 13B illustrate embodiments of various configurations of multi-hole needles.

Other examples of target regions or sites which may exhibit a lower resistance than surrounding regions include open spaces or cavities, or regions of loose tissue surrounded by denser tissue.

In FIGS. 14A, 14B, 14C and 14D, a multi-hole needle is deployed into a centrifuge tube contacting two distinct layers of silicone, separated by a very thin gap, representing a target cavity within tissue. Irrespective of the exact location of the holes relative to the gap, the injected red dye is delivered exclusively to the narrow cavity between the two blocks of silicone. In this case the surrounding silicone offers sufficient mechanical resistance to allow fluid to be effused only from the hole exposed to the cavity.

Similarly, when a multi-hole needle, full of liquid and/or gas, is placed across a membrane that has a pressure differential, upon injection, the liquid is seen to largely infuse into the area of lower pressure (see FIG. 15).

In another embodiment of the multi-hole needle, each hole is individually exposed to an orifice in an inner tube through which the drug is to be injected (the inner tube is plugged at the distal end). The physician exposes one hole at a time, starting in a distal to proximal fashion, until the physician feels a drop in resistance and is able to infuse (see FIG. 16). The same setup can be used to introduce a catheter through each hole until it enters without resistance indicating it is in a fluid-filled cavity. Similarly, in a simplified approach, the inner element consists of a standard hollow tube. As the hollow tube is retracted from distal to proximal, it sequentially exposes the first hole, then the first and second hole, etc. until a drop in resistance is felt and the physician can infuse the drug.

In a further embodiment of this approach, an adjustable internal wedge is used to angle an internal catheter to be directed out a lateral hole; if resistance is encountered when attempting to extrude the catheter, the wedge is retracted to align with the next lateral hole. An attempt is again made to extrude the catheter, and this process is repeated in a distal to proximal fashion, until the catheter is inserted into the cavity of low resistance.

The leading edge of the needle and device embodiments described above may be a pencil point or may be a double bevel needle point, or may be any suitable needle point or leading edge. In some embodiments, the leading edge is closed, that is, the distal tip of the needle or other penetrating element does not have an opening to a lumen.

In some embodiments, the lumen may extend only partially along the device, or may be entirely outside of the device. In such an embodiment, the lumen openings may be lumen extensions which extend from a common lumen and extend to a sidewall of the device. For example, a lumen may be positioned distal to the penetrating portion of the device and include three lumen extensions which reach the sidewall of the penetrating portion at different longitudinal positions along the penetrating device. In this manner, the lumen has three openings which receive the same fluid pressure when pressure is applied to the lumen fluid.

2.1.1.2 Multi-Hole Needles with Adjustable Sensitivity

Needles which have a tunable sensitivity offer useful advantages in targeted drug delivery. For example, in FIG. 17, a multi-hole needle is illustrated which has an inner element with corresponding holes that can be rotated to adjust the pressure required to infuse using the needle. The physician starts with no overlap and applies a constant infusion pressure. The inner element is then gradually rotated until the drug begins to infuse. This helps maximize the capacity of the needle to inject into a low pressure cavity.

In another embodiment, the holes are offset in a spiral fashion. In the case where the holes are in a spiral configuration, a catheter is introduced through each hole until it enters without resistance indicating it is in a fluid-filled cavity.

Another embodiment of this concept is illustrated in FIG. 18. In this case, the holes in the inner element are covered by cantilever-like elements. When the inner element is rotated relative to the outer element, which has a corresponding longitudinal slot, more of the cantilever elements are exposed. Once a sufficient amount of the cantilever beam is exposed to overcome the resistance of the surrounding tissue, the holes in the inner element open. If the needle is placed through a pocket of low resistance, the corresponding cantilever is the first to open, allowing exclusive injection into that space.

2.1.1.3 Multi-Hole Needles with Breakable Element

Another method of promoting selective injection through a multi-hole needle is illustrated in FIG. 19. Here, each hole is covered with a highly distensible non-porous membrane of pliable material. When infusing pressure is applied internally, the membranes begin to expand. The membrane in the pocket of least resistance expands the fastest. This membrane expands to a point of failure, or may be intentionally ruptured as it contacts a sharp edge at a threshold point.

2.1.2 Changes to Viscosity of Therapeutic Agent

The capacity and speed at which a liquid is able to flow into an area of reduced resistance is influenced by its viscosity. Whereas as a low viscosity liquid may tend to move freely from the needle into the surrounding tissue once infusion pressure is applied, a higher viscosity liquid will move at a slower rate and tend not to disperse into the surrounding tissue. For this reason, by varying the viscosity of the solution, more efficient delivery of the therapeutic agent to a potential space may be achieved.

2.1.3 Dual Lumen Needle with Balloon Indicator and Separate Delivery Channel

In FIG. 20, one embodiment of selective delivery to a cavity of less resistance is illustrated. According to this embodiment, a dual lumen assembly is provided. One lumen is connected to a pressure sensitive balloon. The other lumen is connected to a separate syringe that infuses through a separate orifice at the same longitudinal position once the balloon has been correctly placed. The balloon is free to inflate when the principal channel is pressurized at atmospheric pressure. The needle is inserted into the tissue with the balloon deflated. The balloon is then pressurized such that the needle is still free to pass through the tissue without additional resistance—this channel is held at this pressure (e.g., syringe is locked) and the needle is advanced further. The balloon expands once the cavity of lower pressure is entered. The expanded balloon provides a tactile feedback to the user by providing resistance when the user pulls lightly on the needle. The supporting stylet is then removed from the secondary infusion channel and the desired medium is infused, secondary to aspiration if necessary. As will be apparent to one of skill in the art, the fluid used to inflate the balloon (or other membrane) may be a gas or a liquid.

One embodiment of a balloon element of this device is shown in FIG. 21. In other embodiments, instead of providing a secondary channel, the balloon is configured to be porous once expanded or to have a central lumen through which the injection can be made, without the need for a secondary channel.

Any suitable type of membrane, such as a balloon or other material, may be used in some embodiments. A single membrane covering multiple openings may be used in some embodiments, or separate membranes for each opening may be used. A membrane may cover an opening by being positioned on the outside of the opening, the inside of the opening, or intermediate the outside and inside of the opening.

2.2 Needle Uses

In each of the above embodiments, drugs may be delivered through the needles in liquid form, or as a suspension of micro-particles or nano-particles containing a drug. A suspension of micro-particles or nano-particles may delivered for use with imagine application instead of, or in addition to, the delivery of a drug. For example, imaging and/or contrast agents may be delivered by devices and methods disclosed herein. Additionally, the above needle designs can be used to deliver cells, organoids, or tissues. Various embodiments also may be used for biopsy or sensing purposes. Embodiments disclosed herein may be used to infuse vitamins, biomaterials, proteins, cells (e.g., stem cells or progenitor cells), peptides, RNAi, inorganic materials, polymers, hydrogel materials, hyaluronic acid, and/or lubricating materials. Further applications include the placement of fillers or aesthetic altering agents for dermatology and or cosmetic applications.

In some embodiments, embodiments described herein may be used to withdraw fluids, such as liquids, from a body. For example, a vacuum may be applied to a multi-opening needle, and one or more openings that are subjected to a higher pressure than other openings may selectively pass liquid to a lumen, while the openings subjected to a lower external pressure pass limited or no liquids.

Various devices and methods described herein do not necessarily need to be used for infusing or withdrawal of fluids. In some embodiments, the devices and methods may be used for detection or certain tissues, tissue regions and/or tissue spaces.

Various types of openings may be used with embodiments herein, including slits, holes, and/or tapered opening (e.g. pyramid shaped, cone shaped, or telescoping). Opening may be patterned or meshed in some embodiments, and also may be nano-scale, micro-scale or macro-scale.

In some embodiments, a lumen opening may be formed with a region of porous material. For example, the needle or other tube may include two or more regions with an increased porosity which permits fluid to escape or enter a lumen. In some embodiments, the entire tube may have a porous wall, and various regions may have different porosities. The tube may be porous on a micron scale or a nano scale in some embodiments.

Target sites for one or more of the above-described embodiments may include, but are not limited to, blood vessels, degenerated discs (e.g., during kyphoplasty procedures), joints, fat, lungs (including collapsed lungs). Embodiments may be used as part of a tracheotomy procedure, placement of gastric tubes, and withdrawing fluid from cysts or the peritoneal cavity. Methods and devices disclosed herein also may be used to target a medical implant, or to access a region of the brain or a tumor (e.g., at the necrotic nerve).

Further applications include industrial applications with larger penetrating elements and tubes. For example, a multi-opening pipe may be used to inject cement or withdraw oil. For injecting cement, when one or more of the openings reaches a region of lower pressure, cement may be injected. For withdrawing oil, when one or more of the opening reaches an area of higher pressure, oil may be drawn into the tube. Of course, embodiments disclosed herein may be used for other non-medical applications as well. Embodiments disclosed herein may be used for short term application and/or long term application. For example, embodiments may be used for cannulation or implantation.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method of infusing a fluid comprising:
providing a penetrating element and a tube having a lumen and a plurality of lumen openings spaced longitudinally along a sidewall of the tube lumen;
penetrating the penetrating element into a body;
positioning the tube such that at least one of the lumen openings is positioned in a target region at the same time that at least one of the openings is not positioned in the target region;

providing fluid to the lumen;

pressurizing the fluid in the lumen to a first pressure which forces the fluid to exit the lumen through the at least one of the lumen openings that is positioned in the target region; and the first pressure is insufficient to force the fluid to substantially exit the one or more lumen openings that are not positioned in the target region;

wherein the target region has a first external pressure external to the penetrating element, and a region in the body that covers the one or more lumen openings that are not positioned at the target region has a second external pressure; and the first external pressure is lower than the second external pressure.

2. The method of claim 1, wherein the penetrating element forms the tube.

3. The method of claim 1, wherein the plurality of lumen openings are positioned along on a sidewall of the penetrating element.

4. The method of claim 1, wherein the penetrating element comprises a closed sharp distal tip.

5. The method of claim 1, further comprising:

sliding an inner element within the penetrating element, the inner element comprising a lumen opening;

and aligning the inner element lumen opening with a first penetrating element lumen opening.

6. The method of claim 1, further comprising:

sliding an inner element within the penetrating element, the inner element comprising a plurality of lumen openings;

aligning a first inner element lumen opening with a first penetrating element lumen opening; and aligning a second inner element lumen opening with a second penetrating element lumen opening.

7. The method of claim 1, wherein the target region is a synovial sac.

* * * * *